United States Patent [19]

Winter

[11] Patent Number: 4,998,268
[45] Date of Patent: Mar. 5, 1991

[54] APPARATUS AND METHOD FOR THERAPEUTICALLY IRRADIATING A CHOSEN AREA USING A DIAGNOSTIC COMPUTER TOMOGRAPHY SCANNER

[76] Inventor: James Winter, 15145 Mulholland Dr., Los Angeles, Calif. 90077

[21] Appl. No.: 308,266

[22] Filed: Feb. 9, 1989

[51] Int. Cl.[5] .................. A61B 1/00; G21K 1/02; G21K 1/04
[52] U.S. Cl. ..................................... 378/63; 378/4; 378/64; 378/147; 378/150; 378/151; 378/152
[58] Field of Search .................. 378/64, 65, 68, 69, 378/149, 151, 150, 148, 147, 146, 63, 4, 156, 152

[56] References Cited

U.S. PATENT DOCUMENTS

| | | | |
|---|---|---|---|
| 4,118,631 | 10/1978 | Froggatt | 378/65 |
| 4,200,799 | 4/1980 | Saito | 378/150 |
| 4,266,139 | 3/1981 | Sportelli et al. | 378/65 |
| 4,365,341 | 12/1982 | Lam | 378/65 |
| 4,598,415 | 7/1986 | Luccio et al. | 378/119 |
| 4,766,603 | 8/1988 | Okabe et al. | 378/150 |

FOREIGN PATENT DOCUMENTS 1029827 3/1980 Japan .................. 378/151

Primary Examiner—Janice A. Howell
Assistant Examiner—Don Wong
Attorney, Agent, or Firm—Matthew F. Jodziewicz

[57] ABSTRACT

In combination with a diagnostic CT scanner using radiant energy for imaging, an apparatus for therapeutically irradiating a target, comprising a mask that partially attenuates the radiant energy passing therethrough, but transmits through an aperture sufficient radiant energy for imaging. The mask, intermediate the radiant energy source and the target, passes an unattenuated portion of the radiant energy to irradiate the target. The cross-sectional shape and spatial position of the mask aperture can be selectively varied. A post-mask is aligned with the mask aperture and attenuates the radiant energy passing therethrough to an energy level essentially uniform with that of the radiant energy passing through the mask to permit continued imaging during therapeutic irradiation of the target. A method of using the invention in combination with a diagnostic CT scanner using radiant energy for imaging is also provided.

27 Claims, 5 Drawing Sheets

© 1990 James Winter

© 1990 James Winter

© 1990 James Winter

APPARATUS AND METHOD FOR THERAPEUTICALLY IRRADIATING A CHOSEN AREA USING A DIAGNOSTIC COMPUTER TOMOGRAPHY SCANNER

NOTICE REGARDING COPYRIGHTED MATERIAL

A portion of the disclosure of this patent document contains materials subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND OF THE INVENTION

1. Field of the Invention

This invention relates in general to radiation therapy, and, more particularly, to an apparatus, for use in combination with a diagnostic computer tomography (CT) scanner that uses a radiant energy beam for imaging purposes, for permitting the therapeutical irradiation of a chosen area with the radiant energy beam.

2. Description of the Related Art

Prior use of the diagnostic computer scanner limited the use of its radiant energy beam to imaging purposes. A patient was placed within the scanner gantry and sequential scanning of the patient commenced using the radiant energy beam of the scanner to provide a series of images representing the internal structure of the patient without the need for intrusive surgery.

If the images derived from the scanning procedure indicated that radiation therapy of a particular area of the patient was desirable, several possibilities were available. In any event, however, in each of these possibilities the patient was normally removed from the scanner upon conclusion of the scanning procedure and radiation therapy was performed upon a second apparatus designed specifically for radiation therapy procedures.

The reason a second apparatus is normally employed is due to the fact that the radiation energy levels necessary for radiation therapy are incompatible with those levels used in scanning a patient. Radiation therapy calls for radiation energy levels capable of destroying target tissue, while scanning for imaging purposes uses radiation energy levels held at a much lower level to prevent the destruction of tissue during the scanning and imaging procedure itself. Thus, many consider the two procedures to be incompatible upon the same apparatus.

The use of two devices results in physical difficulties in successfully re-positioning the patient and locating the position and extent of the target area to be therapeutically irradiated. This fact, along with the additional fact that physical changes may have occurred to the patient during the time interval between the imaging and therapy procedures, all cause considerable problems in guarantying a successful procedure for the patient at a minimum of danger and discomfort.

The present invention overcomes not only these problems, but does so at a considerable lessening of the danger and risk to the patient undergoing such radiation therapy.

The present invention can be used in combination with existing diagnostic computer tomography scanners, thus enabling an existing apparatus, presently in widespread use, to add a therapeutic dimension to its purpose at little modification and small cost. Radiation therapy may therefore be provided by medical centers previously unable to do so due to the expense of purchasing, installing and operating a separate radiation therapy device.

In addition, the present invention provides a number of benefits over existing radiation therapy devices.

Specifically, in comparison with a gamma knife radiation therapy device, the present invention provides a more flexible geometry, and thus a more flexible irradiated target volume size and shape for radiation purposes. Likewise, since the present invention can be used in combination with existing computer tomography scanners, it has a lower cost and weight than the gamma knife. Unlike the gamma knife, the present invention provides a diagnostic imaging capability, and the lower x-ray energy used in the present invention utilizing a scanner unit allows for iodine dose enhancement of the target area. Also imaging of the patient may occur contemporaneous with the radiation therapy procedure, thus allowing real time monitoring the position of the target area chosen for irradiation. Thus the present invention provides for more accurate localization of the area to be irradiated than prior art use of the gamma knife as a standalone radiation therapy unit. The present invention also does not require any stereotactic device for more precise positioning than that of the gamma knife. Finally, the present invention uses a lower x-ray energy level that allows a higher RBE, thus lessening the total dose requirement needed for successful radiation treatment and improving the dose profile due to the continuous rotation and increased number of radiation fields provided by utilization of a scanner unit that are not found in the gamma knife presently in use for radiation therapy procedures.

Another apparatus currently in use for radiation therapy procedures is the radiation therapy unit using either cobalt, a linear accelerator or orthovoltage to produce its radiant energy beam.

Likewise, over the radiation therapy unit, the present invention provides for stereotactic localization and more accurate positioning of the patient due to the fact that a single device having diagnostic imaging capability is used for both imaging and therapy purposes, The present invention thus eliminates the need for patient movement and repositioning by providing for real time patient imaging contemporaneous with the radiation therapy for monitoring the target area location and position with respect to the radiation beam.

The present invention also provides for a more flexible geometry for the chosen target area. The present invention is also found in a device that has a lower cost and weight than the radiation therapy units in common use today.

Another positive aspect of the present invention over that of existing radiation therapy units is that the x-ray tube used in most computer tomography scanners provides a higher dose rate than either cobalt or other isotopic sources of radiant energy. The present invention also provides for more accurate localization of the effects of the radiant energy beam, while the lower x-ray energy level allows for iodine dose enhancement of the target area and a higher RBE, thereby lessening the total radiation dose requirement. The CT scanner gantry tilt capability of the present invention is much more flexible geometrically than available with linear accelerators used for radiation therapy. Finally, the present invention provides for an improved radiation dose profile over that of radiation therapy units due to a continuous rotation of an increased number of fields providing the radiation beam.

The prior art includes the use of variable collimators for radiation therapy, but not in connection with diagnostic CT scanners as in the present invention.

SUMMARY OF THE INVENTION

In general the present invention can be embodied in an apparatus and a method for use with a diagnostic computer scanner that uses a radiant energy beam for imaging purposes.

An apparatus embodying the present invention finds use in combination with a diagnostic computer tomography scanner that uses a radiant energy beam for imaging purposes. The apparatus is useful for therapeutically irradiating a chosen area with the radiant energy beam and comprises a masking member fabricated from a material that partially attenuates the radiant energy passing therethrough, but transmits a sufficient amount of the radiant energy for imaging purposes.

The masking member has an aperture therein adapted for passing an unattenuated portion of the radiant energy beam therethrough. The masking member is removably fastened to the scanner, interposing the masking member in the radiant energy beam intermediate the source of the radiant energy beam and the chosen area for passing an unattenuated portion of the radiant energy beam to irradiate the chosen target area.

The cross-sectional shape of the masking member aperture can be selectively varied in a predetermined manner as a function of the location of the chosen area and the position of the source of the radiant energy beam.

The spatial position of the masking member aperture can also be selectively varied in a predetermined manner as a function of the location of the chosen area and the position of the source of the radiant energy beam.

A post-masking member is aligned with the masking member aperture and fabricated of a material that attenuates the radiant energy passing therethrough to an energy level essentially uniform with that of the radiant energy passing through the masking member to permit continued imaging during therapeutic irradiation of the chosen target area.

The present invention is also found embodied in a method for using a diagnostic computer tomography scanner that uses a radiant energy beam for imaging purposes for therapeutically irradiating a chosen area with the radiant energy beam.

This method comprises the steps of positioning a patient in the scanner using positioning restraints to prevent patient motion with respect to the scanner. A diagnostic scan of the patient is performed and an area is chosen for therapeutic irradiation. The patient is repositioned as necessary to move the chosen area to a selected predetermined location. The spatial dimensions of the chosen area are measured. A masking member fabricated from a material that attenuates the radiant energy passing therethrough and having an aperture therein adapted for passing an unattenuated portion of the radiant energy beam therethrough with a cross-sectional beam area essentially equal to that of the chosen area is selected. The masking member is interposed in the radiant energy beam intermediate the source of the radiant energy beam and the chosen area so that the unattenuated portion of the radiant energy beam irradiates the chosen area. The chosen area is scanned through multiple cycles to irradiate the chosen area to a desired exposure level. A post-masking member is maintained in alignment with the masking member aperture and is fabricated of a material that attenuates the radiant energy passing therethrough to an energy level essentially uniform with that of the radiant energy passing through the masking member to permit continued imaging of the patient during irradiation of the chosen area. The cross-sectional area of the masking member aperture is varied selectively in relation to the location of the chosen area and the source of the radiant energy beam.

The novel features of construction and operation of the invention will be more clearly apparent during the course of the following description, reference being had to the accompanying drawings wherein has been illustrated a preferred form of the device of the invention and wherein like characters of reference designate like parts throughout the drawings.

DESCRIPTION OF THE PREFERRED EMBODIMENTS

Figure 1:
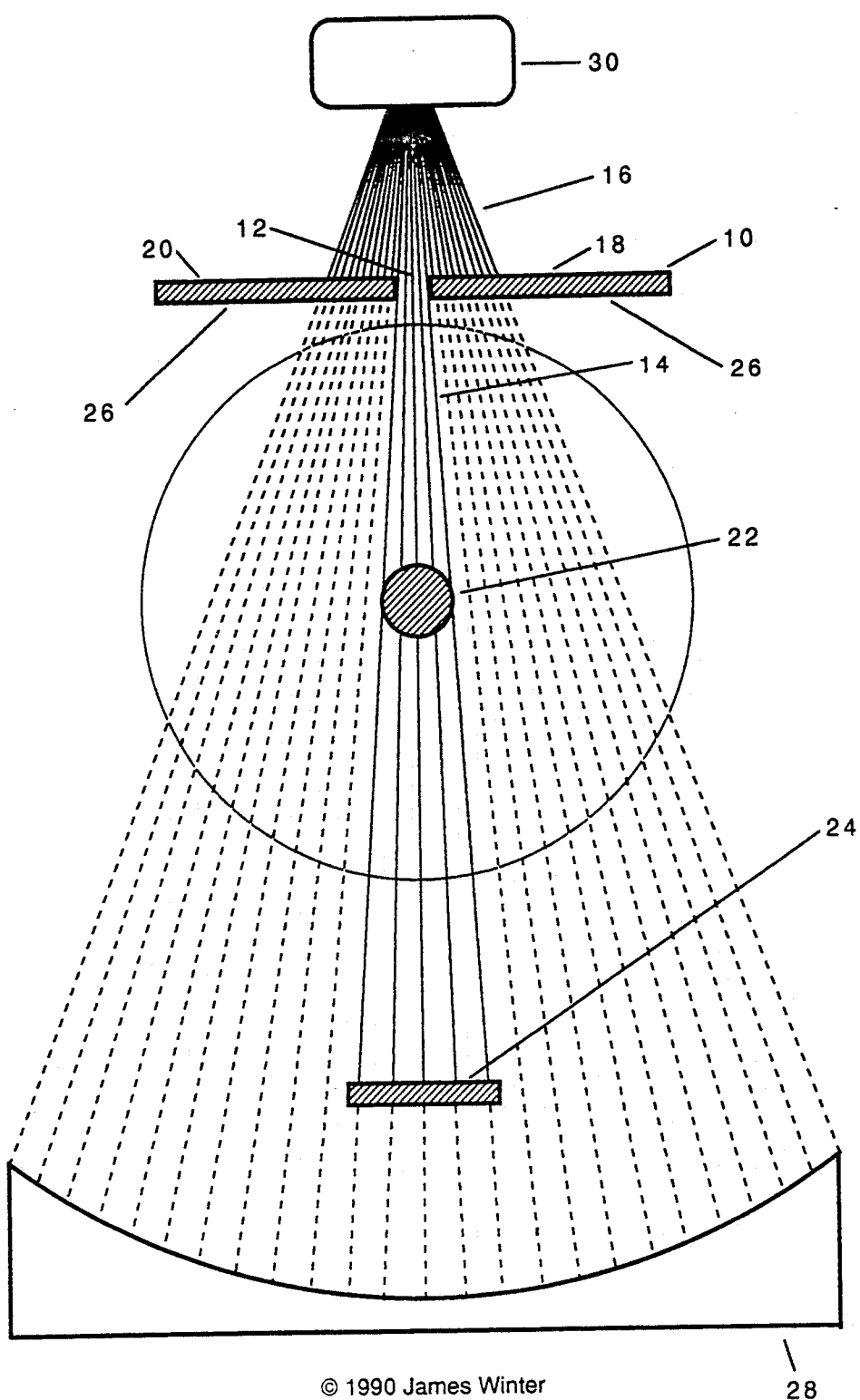
FIG. 1 is a diagrammatic illustration of the present invention to provide imaging during radiation therapy using a radiation beam that can penetrate both a masking member and a post-masking member.

In general, the present invention provides a simple mechanism to use with a conventional diagnostic x-ray computed tomography (CT) scanner to stereotactically therapeutically irradiate a target lesion, symmetrical or non-symmetrical, placed at a given spatial location with regard to the scanner's radiation beam, for example, at the CT scanner's rotation isocenter.

The invention provides an attachment means for a masking member that is modified to connect to a particular CT scanner model and holds interchangeable members having apertures of varying cross-sectional shape. Alternatively, each masking member may have its own attachment means. Registration pins or other mechanism ensure accurate position of the masking member with regard to the target area.

Attachment of the masking member can be anywhere between the x-ray tube and the gantry shroud, for example to the x-ray tube housing adjacent to the window, to the existing slice thickness collimator mechanism, to a bowtie filter, or elsewhere. It must remain stationary with respect to the x-ray tube during rotation and gantry tilt. The specific design will depend upon the mechanical design and available space for each particular model of CT scanner.

A set of therapeutic masking members which restrict the aperture to the central portion of the CT scanner beam when held in position by the attachment means. The masking members are preferably in graded sizes and shapes to be selected to vary the target volume to be therapeutically irradiated. The masking members may have apertures that are round, rectangular or other cross-sectional shape. For example, a therapeutic masking member could be fashioned from a piece of metal of sufficient thickness to stop essentially all of the radiation emitted by the x-ray tube, with a round or a square hole in the center with a diameter of 1 centimeter. When in place, the masking member's aperture is aligned with the x-ray central beam which passes through the rotation and gantry tilt isocenter.

The CT scanner cannot be used for imaging the entire cross-sectional anatomy when the therapeutic masking members are in place. Depending upon the particular CT scanner's performance, an image limited to the small area of the treatment may be produced with the therapeutic masking member in place. If the scanner aborts its operation with the therapeutic masking member in place, it will be necessary to override the abort. This is usually achieved by operating the CT scanner in its "maintenance" mode, intended for use by service personnel.

As an option, described in greater detail below, a set of imaging masking members of identical shape to the therapeutic masking members but made of a different material such as plastic that is only slightly absorbant of radiation. Alternatively, the imaging collimators could be complementary to the therapeutic masking member, that is, thin except at the locations corresponding to the therapeutic masking members's aperture where the complementary imaging collimator is thick. The imaging collimator can be substituted for the corresponding therapeutic masking member and a CT image scan performed. The result will be an artifact superimposed upon the full area cross-sectional image which can be used to verify the location and size of the treatment target volume.

The size of the masking member can be calibrated to take into account beam divergence to the rotation isocenter of the CT scanner, so that the masking member having an aperture marked "1 cm." irradiates a diameter of 1 cm. at the rotation isocenter of the scanner.

Finally, as will be described better in the preferred embodiment of a method that includes the present invention, to treat a target lesion, place the patient in the CT scanner with positioning restraints to prevent patient motion with respect to the scanner's tabletop. A conventional diagnostic scan and repositioning of the patient as necessary is performed, side to side, and by adjusting the table position in or out, and up or down to move the target lesion to the rotation isocenter, the distance to the isocenter as determined by conventional use of the CT scanner's image display location measurement software. The target lesion diameter is measured and the corresponding pair of therapeutic masking members and imaging collimators are chosen. If desired, the imaging collimator is put in place in the attachment mechanism of the CT scanner and a CT scan (or optionally multiple scans with varying gantry tilt angles) to verify the correct size of the masking member aperture and correct positioning of the patient. Full area cross-sectional imaging may be repeated periodically to check for patient motion and mispositioning. The masking member having the correct size aperture is then chosen and attached to the CT scanner. If imaging with the imaging collimator has been performed, replace the imaging collimator with the corresponding therapeutic masking member. Without patient motion, repeatedly scan a large number of times with or without varying gantry tilt and/or slight table motion, according to the therapeutic prescription. For example, 100 scans through the target lesion, each scan delivering 3 rads/scan can deliver 300 rads to the target lesion in under one hour using a conventional CT scanner, while allowing adequate time for x-ray tube cooling.

Specifically, then the present invention is found in combination with a diagnostic computer tomography scanner that uses a radiant energy beam for imaging purposes, and is in a preferred apparatus for therapeutically irradiating a chosen target area with the radiant energy beam embodying the present invention as shown in FIG. 1 comprised with a masking member 10 fabricated from a material that attenuates radiant energy passing therethrough.

The masking member has an aperture 12 therein adapted for passing an unattenuated portion 14 of the radiant energy beam 16 therethrough.

Means, not illustrated, are provided for removably fastening the masking member 10 to the scanner. Preferred means are screws, clips, fasteners, snaps and the like which are capable of holding the masking member in a known and fixed relation to the radiant energy beam but which still permit the removal of the masking member when desired to substitute a new masking member or to remove the masking member altogether for imaging purposes.

The masking member is interposed in the radiant energy beam intermediate the source 30 of the radiant energy beam and the chosen target area 22. Positioning the masking member in this manner provides for passing the unattenuated portion 14 of the radiant energy beam 16 through aperture 12 to irradiate the stet chosen target area.

Means are provided for selectively varying the cross-sectional shape of the masking member aperture to a more complex cross-sectional shape in order to more exactly conform the radiation to the shape of the chosen target area. For example, as described better below, an iris mechanism could be used for a circular or more complex masking member aperture shape.

In one preferred embodiment, such means comprises having the masking member be an iris apparatus with means for selectively varying the cross-sectional shape of the masking member aperture 12. Such means for selectively varying the cross-sectional shape of the masking member aperture 12 are well known in the art and may comprise any of a number of known mechanisms for controlling the iris apparatus.

In an alternate preferred embodiment, masking member 10 comprises at least one pair of spaced opposed jaws 18, 20. Each pair of jaws 18, 20 are selectively adjustable as to spacing between its respective jaws. The means for selectively varying the cross-sectional shape of the masking member aperture 12 in this embodiment comprises a mechanism for selectively controlling the spacing between jaws 18, 20.

In another alternate preferred embodiment, masking member 10 comprises a first and second pair of spaced, opposed jaws. One pair of jaws would have a spacing between the jaws representing the usual slice thickness of a standard collimator found in a computed tomography scanner unit. The other pair of jaws having a spacing that provides the axial width of the unattenuated radiation beam 14. In other words, this second pair of jaws would control the chosen target area irradiation as shown in the FIGS. 1-5.

The actual jaw members of the axial or second pair of jaws may be implemented as a set of strips or pins which extend or retract perpendicular to the axial plane of the scanner device as needed to either open or close the resulting aperture for the unattenuated portion of the radiation beam.

Each pair of jaws is selectively adjustable as to spacing between its respective jaws and is aligned with one another to form the masking member aperture 12 by common spacing between each pair of jaws. In this embodiment, means for selectively varying the cross-sectional shape of the masking member aperture 12 comprises a mechanism for selectively controlling the spacing between respective jaws of each individual pair of jaws.

The mechanism for selectively controlling the spacing between respective jaws of each pair of jaws preferably operates independently on each pair of jaws to control the spacing between respective jaws of each pair.

The preferred apparatus being described also includes means for selectively varying the cross-sectional shape of the masking member 12 aperture in a predetermined manner as a function of the location of the chosen area and the position of the source of the radiant energy beam 16.

Also included in the apparatus being described is means for selectively varying the spatial position of the masking member aperture in a predetermined manner as a function of the location of the chosen target area and the position of the source of the radiant energy beam.

In both of these cases, a computer controlled mechanism may be used to control the spacing between the jaws so as to vary the spacing with respect to either the location of the spatial position of the masking member aperture or of the chosen area with the position of the source of the radiant energy beam. Such computer controlled mechanisms are well known in the art and are found in numerically controlled machines used in manufacturing for example.

In one preferred embodiment, the masking member 10 is fabricated from a material that attenuates essentially all of the radiant energy passing therethrough as shown in FIGS. 2-5. In this embodiment, there is a single unattenuated portion 14 of the radiant energy beam 16 that passes through the aperture 12 of masking member 10 to irradiate the chosen target area of the patient However, it is also preferred in another alternate embodiment shown in FIG. 1, that masking member 10 be fabricated from a material that partially attenuates the radiant energy passing therethrough, and transmits a sufficient amount of the radiant energy for imaging purposes through the solid portion 26 of masking member 10.

In this last embodiment, a post-masking member 24 is preferably aligned with masking member aperture 12 and is fabricated of a material that attenuates the radiant energy passing therethrough to an energy level essentially uniform with that of the radiant energy passing through the masking member 10. In this manner, scanner detectors 28 aligned with the radiant energy beam 16, may continue to provide imaging during the radiation therapy procedure. This would ensure the continued positioning of the chosen target area 22 during the radiation therapy procedure and avoid any changes in position that may have occurred due to either movement of the patient or false initial positioning of the patient prior to the commencement of the procedure. This post-masking member 24 is not required for treatment. Its purpose is to assist in imaging by compensating for the non-uniform irradiation due to the masking member 10 on the scanner imaging detectors 28. If the dynamic range of the scanner imaging detectors 28 will permit, the post-masking member 24 can be omitted and the variation in intensity due to the masking member 10 can be corrected by the imaging computer of the scanner unit prior to reconstruction of the received image.

Figure 2:
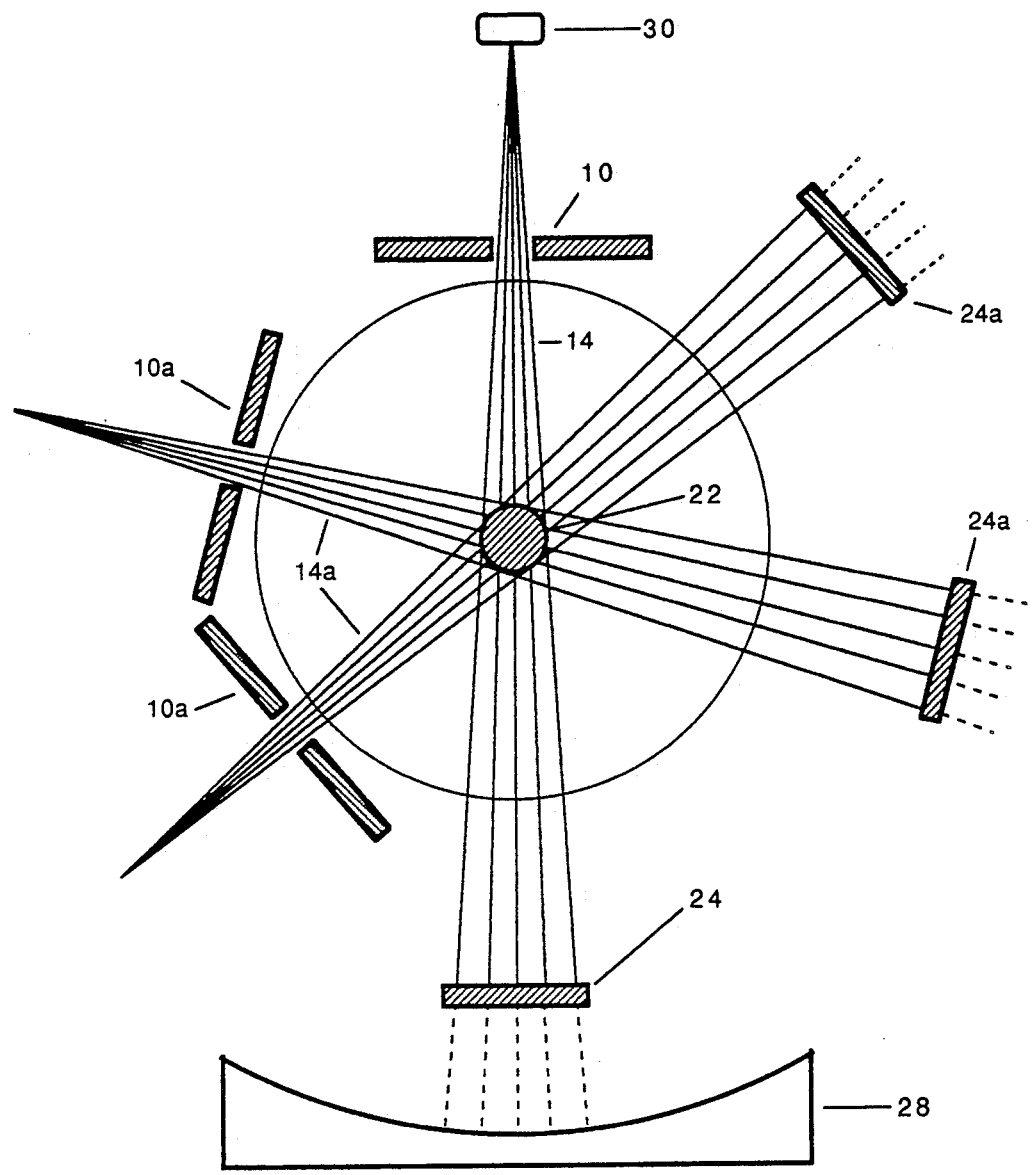
FIG. 2 is a diagrammatic illustration of the present invention embodied with fixed, adjustable masking members to therapeutically treat a target lesion placed at the isocenter of rotation of a CT scanner.

The present invention may also be embodied in a structure as shown in FIG. 2 wherein fixed masking member or members 10 may be employed with adjustable masking members 10a to therapeutically treat a target lesion 22 placed at the isocenter of rotation of a CT scanner. Similar to the discussion above concerning the use of a post-masking member 24 in conjunction with fixed masking member 10, post-making members 24a would be preferably associated with adjustable masking members 10a. Likewise, source 30 and scanner imaging detector 28 are as described above in FIG. 1.

Figure 3:
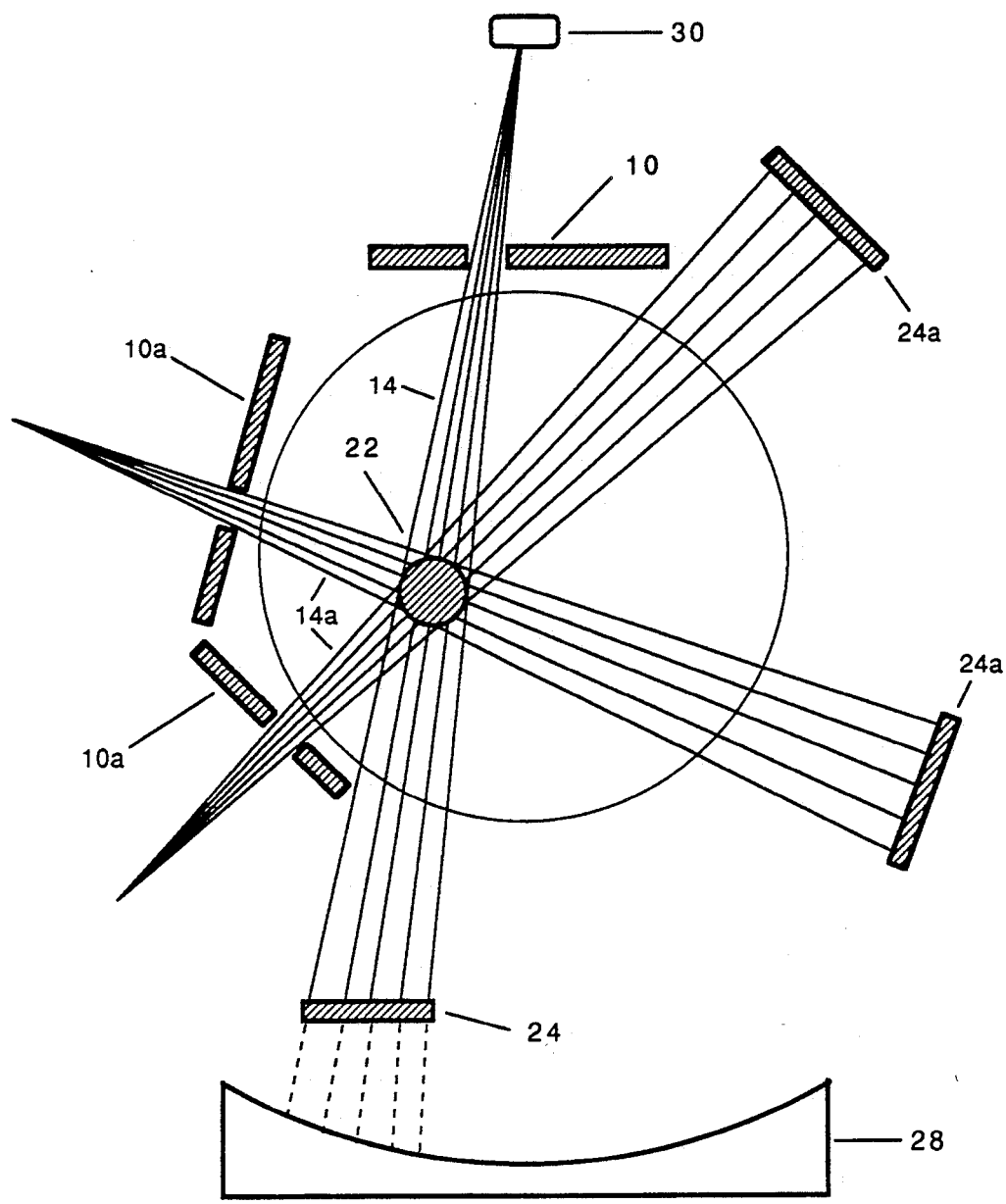
FIG. 3 is a diagrammatic illustration of the present invention embodied with masking members having variable apertures to therapeutically treat a target lesion placed off the isocenter of rotation of a CT scanner.

FIG. 3 illustrates an embodiment of the present invention similar to the that discussed above for the present invention as shown in FIG. 2. In FIG. 3, a preferable embodiment has masking members 10 with variable apertures therein to therapeutically treat a target lesion 22 placed off the isocenter of rotation of a CT scanner.

Figure 4:
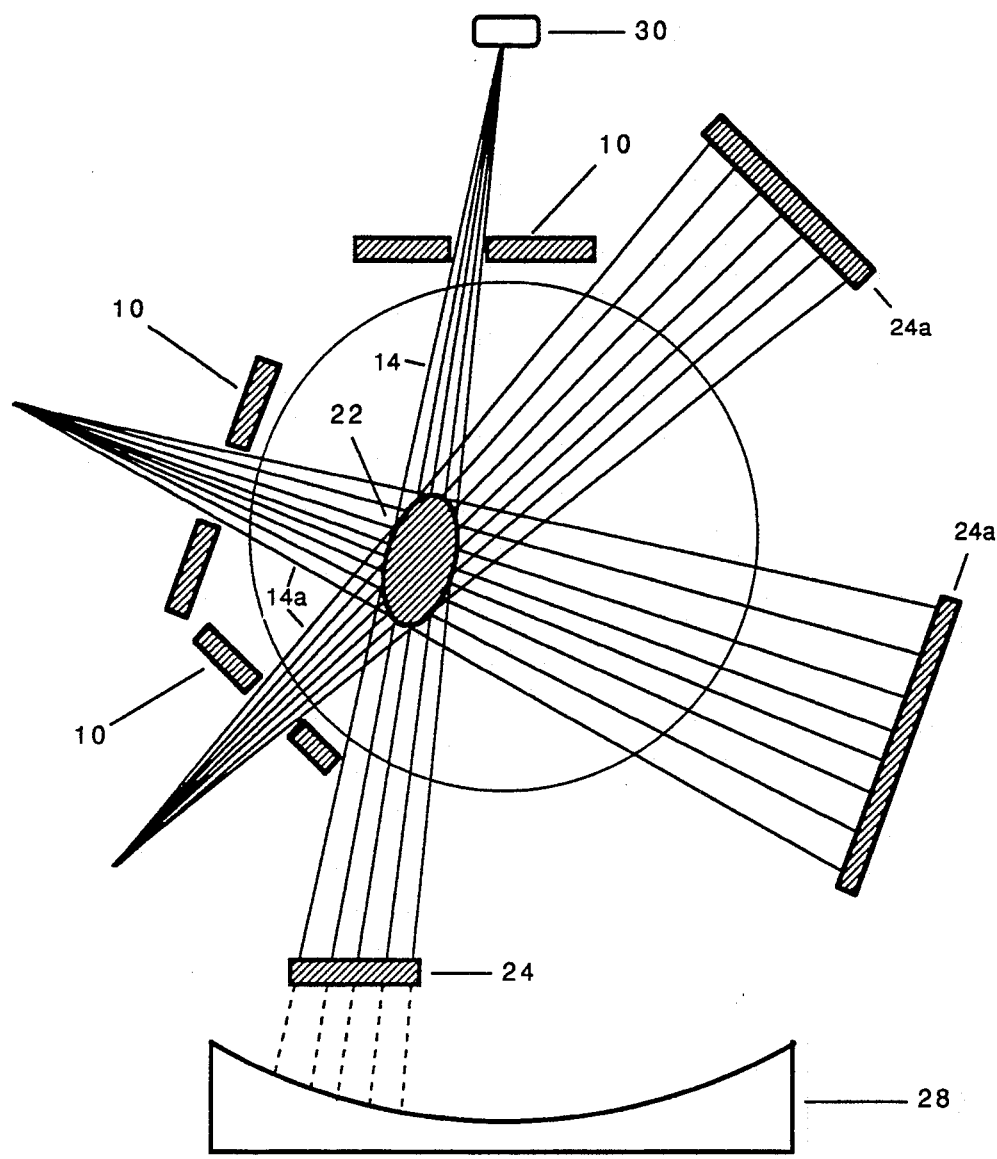
FIG. 4 is a diagrammatic illustration similar to that of FIG. 3 wherein the target lesion is irregular in volume and size; and, FIG. 5 is a diagrammatic illustration of the present invention embodied with triple x-ray tube sources, masking members and a single set of CT scanner imaging detectors on a single gantry to achieve a high dose rate.

FIG. 4 is similar to the structure of FIG. 3, but shows the target lesion 22 as being irregular in both volume and shape. The shown masking members 10, post-masking members 24, as well as scanner imaging detector members 28 and the source 30, are similar to those discussed above for FIG. 1.

A method embodying the present invention would also occur in combination with a diagnostic computer tomography scanner that uses a radiant energy beam for imaging purposes, and an apparatus for therapeutically irradiating a chosen area with the radiant energy beam. The preferred method would comprise the steps of positioning a patient in the scanner using positioning restraints to prevent patient motion with respect to the scanner. Normally, a patient is placed in a known position on a platform that is surrounded by a rotatable gantry having the radiant energy beams carried thereon with opposed detectors to receive the beams as they pass through varying, but known, portions of the patient.

In this manner, the next step would be performing a diagnostic scan of the patient as is normally done in the prior art.

Once the scan is completed, the appropriate individuals must determine whether radiation therapy is necessary to treat an area, such as a lesion, found during the imaging process. If such an area is determined to be an area chosen for therapeutic irradiation, its geometry must be determined and its location pinpointed for proper therapy.

Once the decision has been made to use radiation therapy and the geometry and location of the chosen area are determined, the patient is preferably repositioned as necessary to move the chosen area to a selected predetermined location. While it is preferable to move the patient so that the area chosen to be irradiated would be located at the isocenter of rotation of the scanner gantry, this is not necessary for the invention. By proper control over the apertures in the masking member or members, an area may be irradiated by the radiant energy beam that is not at the isocenter of rotation of the scanner gantry. Such control may be provided by computer control of the apertures of the masking members in selected variation of either the size of the aperture or its location with respect to the source of the radiant energy beam.

Once positioned, a masking member is chosen to complement the geometry of the area chosen for irradiation.

The masking member is interposed in the radiant energy beam intermediate the source of the radiant energy beam and the chosen area so that said unattenuated portion of the radiant energy beam irradiates the chosen area. The chosen area is scanned through multiple cycles to irradiate the chosen area to a desired exposure level.

As was discussed above, it is preferable that the masking member chosen for use in this method be fabricated from a material that partially attenuates the radiant energy passing therethrough, but that transmits a sufficient amount of radiant energy for imaging purposes. With this in mind, it is also preferable to maintain in alignment with the masking member aperture a postmasking member fabricated of a material that attenuates the radiant energy passing therethrough to an energy level essentially uniform with that of the radiant energy passing through the masking member to permit continued imaging of the patient during irradiation of the chosen area.

The present invention is intended to operate during repetitive scanning of the computed tomography imaging unit with the masking member of the invention in place thereon.

In this mode of operation, the imaging data from a number of rotations would be added together to form the projection data for CT imaging to monitor the radiation therapy procedure in real time. This provides the utility of being able to confirm the correct positioning of the chosen target area during the radiation therapy procedure while minimizing the radiation dose outside the chosen target area.

While commercial CT scanners offer a limited range of imaging slice thicknesses, generally 1.5 mm up to 10 mm in thickness, the present invention could modify the imaging slice thickness by varying the aperture in the masking member to encompass target areas thicker than 10 mm in the orientation perpendicular to the axial plane illustrated in the attached Figures.

The therapeutic beam used for the radiation therapy procedure is expected to be many times more intense than the imaging portion of the radiation beam which reaches the CT unit detectors. The specific choice as to imaging beam strength will be made so as to achieve adequate radiation at the detectors to achieve an image with an acceptable noise level, taking into account the ability of the CT unit to sum the radiation from a number of rotations to obtain the data for a single image. For example, if a single typical diagnostic scan represented 3 rads to the target area, a treatment might consist of 100 scans of the target area, yielding a treatment dose of 300 rads to the target area. If the radiation passing through the masking member, through the body of the masking member, not through the aperture of the masking member, is 1/20 of the radiation passing through the aperture, then an image equivalent in quality to the usual diagnostic scan can be obtained by combining 20 therapeutic scans of the target area. By a moving average, combining the previous "n" number of scans into one image (n=20 in this example), the image could be updated, that is, reconstructed again or refreshed, after each scan to include in the image projection data from the most recent "n" therapeutic scans. By varying the number of scans "n", a tradeoff can be made between image noise and how up to date this image is.

In the simplest case shown in FIG. 2 which illustrates locationally fixed adjustable aperture masking members positioned to treat a target area, for example a lesion, placed at the isocenter of rotation of the CT scanner unit, the patient would be scanned initially while attached to an apparatus which allows adjustment up-down and left-right. The table elevation mechanism of commercial CT scanners fulfills the requirement for an up-down adjustment mechanism. A mechanism such as used for stereotaxic neurosurgery would also suffice.

After the preliminary scan, the coordinates of the lesion or target area are determined relative to the scanner's rotation isocenter by use of the CT scanner's display computer, and the patient is moved in the corresponding distance and direction to bring the target lesion to the isocenter of rotation.

In any case, after the preliminary localization scan, the size and location of the target lesion to be treated is determined by manually or automatically outlining the target lesion on the display screen, by enclosing the lesion in a geometric shape, or by other conventional means. The present invention calculates geometrically the masking member aperture required in each scanner orientation to irradiate the target lesion as the scanner rotates, (and also the table motion, gantry tilt, and masking member aperture required, if three-dimensional radiotherapy is used). The computer can then control the treatment process by adjusting the x-ray output, masking member aperture, table position, and gantry tilt as required to achieve the prescribed treatment to the target lesion area.

Monitoring of the treatment can be by visual observation of the simultaneous imaging. The monitoring of the therapy can also be automated by computer comparison of successive treatment images with an alarm sounded if the image changes. A change in the image could signify a problem with the treatment, such as patient motion. Detection of image change could be by image processing techniques such as integral of the mean squared difference between images, or comparison of image centroids, or motion detection by cross-correlation.

Optimal treatment may be computed by selecting the desired therapeutic x-ray dose distribution, then iteratively varying the masking member aperture (or even the beam intensity across the aperture) in the various orientations until the resultant apertures and corresponding intensities when projected (according to the laws of attenuation of radiation beams) converge upon a solution as close to the desired distribution as can be achieved. It remains to be demonstrated that this would be any better than simply adjusting the masking member aperture to irradiate the entire target lesion in each orientation. Direct mathematical solutions or constrained iterative solutions are also possible. For example, the radiation dose could be constrained so as to minimize the radiation dose (or not exceed a preselected radiation dosage) to a particular sensitive region apart from the target lesion.

As indicated above in the description, if imaging during the therapy procedure is not desired, a thicker masking member can be used so that essentially no radiation enters the patient except through the aperture of the masking member. This could be an option which could be activated or deactivated as desired.

The radiation source could be a rotating anode or fixed anode x-ray tube as shown in the Figures. A fixed anode x-ray tube with oil cooling of the anode generally delivers its radiation dose more slowly than a rotating anode tube, but can operate continuously without interruptions for tube cooling. For this reason, fixed anode x-ray tubes are generally preferred for orthovoltage radiation therapy, because the treatment time is less. The same advantage applies to the present invention if it is being designed as a purely therapeutic machine, as opposed to a dual purpose design used for both diagnosis and therapy for which a rotating anode tube is more advantageous.

The present invention can be designed to be retrofitted on existing diagnostic CT scanners. These scanners can treat to an approximate radiation dose of about 300–400 rads/hour of elapsed time, using a rotating anode tube, including tube cooling time, that is, the equivalent of two spine CT diagnostic exams per hour, but with all the scans being directed at the same target lesion (for example 120 scans/hour × 3 rads/scan = 360 rads/hour).

When gantry tilt is used to achieve three-dimensional therapy, either the scanner table can be moved in the in/out direction to accommodate each gantry tilt angle, or the table can be moved once in the up/down direction prior to the treatment to bring the target lesion to the horizontal level of the isocenter of rotation, so that in/out motion is not needed to accommodate gantry tilt.

A translate-rotate geometry CT scanner, so called "first" or "second" generation CT scanner, can substitute electronic control of the x-ray beam intensity for masking member aperture variation. The treatment time, however, would be greatly prolonged unless the translation were limited to the location of the projection of the target lesion, but that would limit simultaneous imaging during therapy. Alternatively, translation may be slowed at locations resulting in irradiation of the target area.

Short treatment times may require the use of CT scanners and equipment that include a heat dissipating stationary anode, oil cooled tube or high heat capacity rotating anode tube of advanced design to produce the radiation beam.

Figure 5:
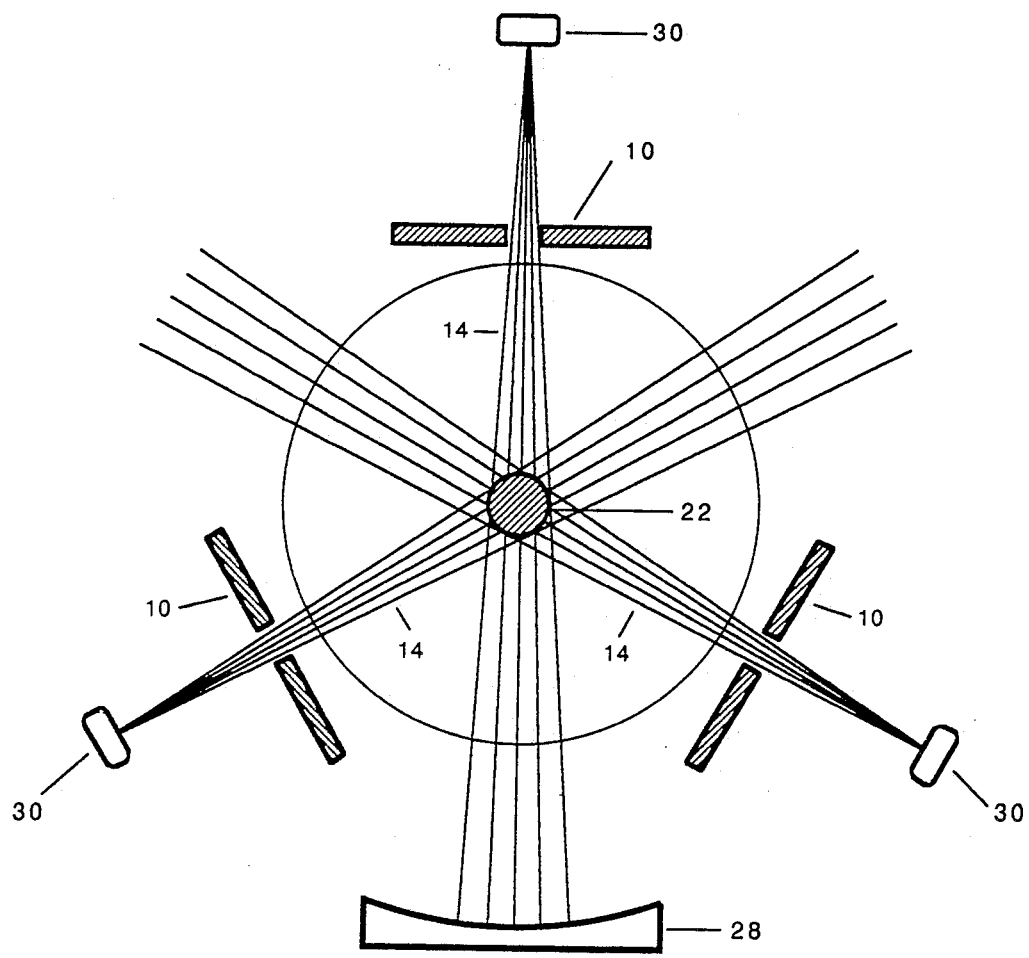

Also preferable is the use of a multiple x-ray tube CT scanner, with several x-ray tubes attached to the scanner gantry to reduce the treatment time required for radiotherapy, for example, a three x-ray tube CT scanner design with the tubes located 120 degrees apart on the gantry as shown in FIG. 5. (Note: An odd number of x-ray tubes angularly spaced equally around the gantry provides weight balance and avoids beam interference since the beams are not colinear; for example, a five x-ray tube design could be used in place of the three x-ray tube design shown in FIG. 5.)

When multiple x-ray tubes are placed on a scanner gantry, they can be of different designs. For example, a rotating anode tube can be used for imaging while oil-cooled stationary anode tubes are used for radiation therapy.

When multiple x-ray tubes are placed on a scanner gantry, only one set of imaging detectors is required for imaging. This results in a lower cost design with no adverse effect on image quality whatsoever.

Alternatively, if the goal, or additional goal, of the design is a very fast CT imager, multiple sets of imaging detectors (one set for each of the multiple x-ray tubes) can be included to speed up the imaging process. For example because less than 360 degree rotation is required to acquire all possible angular projection data (that is, views from every direction of the full 360 degree circle or alternatively fully covering 180 degrees). This has application to stop motion imaging, cardiac imaging, and reduction of respiratory and other motion artifacts.

Additional beam filtration by the use of copper or aluminum in the fabrication of the apertures of the masking members can be used to harden the radiation therapy beams in order to spare the superficial skin and high atomic number bone relative to a deep target lesion of low atomic number. This beam hardening effect, however, is undesirable if iodine dose enhancement of the target area is desired.

In some situations, it may be desirable not to irradiate from particular directions, in order to spare particular anatomic structures. This may be accomplished by closing or restricting the aperture of the masking member, or by turning off the x-ray tube output by turning off the high voltage or use of grid control in the x-ray tube.

An area of special note is that the present invention may also be used to irradiate a target lesion that is not located at the rotation isocenter of the CT scanner. In this case, a close comparison must be made of the dosimetry for irradiation of the same target lesion when moved to the center of rotation versus when irradiated in an eccentric location using movable masking members. Some differences would be expected in this situation due to differing beam attenuation and differing inverse square law effects, but the magnitude of these effects upon dose distribution can be determined.

A high voltage CT scanner using an x-ray therapy tube may be operated at higher kilovoltage for therapy to achieve higher dose rates and greater electron energy to x-ray conversion efficiency with lower percentage x-ray tube heating (for example, 250 kVP) as well as at lower kilovoltage (80–140 kVP) for more optimum imaging contrast.

The beam intensity profile may be modulated along each projection using a translate-rotate type CT scanner with varying mA or kV, or alternatively with a purely rotational scanner by time varying the masking member aperture during each angular projection to better achieve a desired dose distribution. A masking member having its aperture automatically controlled that uses pins or plugs which extend or retract to open or close the masking member aperture would be especially well suited for this latter application.

When therapeutically irradiating a target area using a number of angled planes with varying gantry tilt, it is desirable to omit those x-ray tube irradiation angles coinciding with the axis of gantry tilt so that excessive irradiation does not result along a line through the axis of gantry tilt which represents the intersection of all of the angled planes at varying gantry tilt, that is, when the x-ray beam is horizontal pointed either to the left or to the right. This can be achieved by turning off the x-ray tube at those angles, by closing the aperture of the masking member at those angles, or by means of lead or other stationary blockers placed on both sides of the gantry on the gantry tilt axis. This can also be achieved by an x-ray tube rotation of less than 180 degrees which does not include the horizontal.

The above described and disclosed invention also has industrial applications for the specific irradiation of a given target area by machinery that is not presently primarily constructed for irradiation purposes. Many of these applications will be obvious to those of ordinary skill in the art given the presently disclosed invention.

The invention described above is, of course, susceptible to many variations, modifications and changes, all of which are within the skill of the art. It should be understood that all such variations, modifications and changes are within the spirit and scope of the invention and of the appended claims. Similarly, it will be understood that it is intended to cover all changes, modifications and variations of the example of the invention herein disclosed for the purpose of illustration which do not constitute departures from the spirit and scope of the present invention.

What is claimed is:

1. In combination with a diagnostic computer tomography scanner that uses a radiant energy beam for imaging purposes, an apparatus for therapeutically irradiating a chosen area with the radiant energy beam comprising:
    a masking member fabricated from a material that attenuates radiant energy passing therethrough and having an aperture therein adapted for passing an unattenuated portion of the radiant energy beam therethrough; and,
    means for fastening said masking member to the scanner interposing said masking member in the radiant energy beam intermediate the source of the radiant energy beam and the chosen area for passing said unattenuated portion of the radiant energy beam to irradiate the chosen area.

2. An apparatus for therapeutically irradiating a chosen area with a radiant energy beam as in claim 1, further including,
    means for selectively varying the cross-sectional shape of said masking member aperture.

3. An apparatus for therapeutically irradiating a chosen area with a radiant energy beam as in claim 2, wherein said masking member is an iris apparatus and said means for selectively varying the cross-sectional shape of said masking member aperture comprises a mechanism for controlling said iris apparatus.

4. An apparatus for therapeutically irradiating a chosen area with a radiant energy beam as in claim 2 wherein said masking member comprises at least one pair of spaced opposed jaws, said pair of jaws selectively adjustable as to spacing between its respective jaws and said means for selectively varying the cross-sectional shape of said masking member aperture comprises a mechanism for selectively controlling the spacing between said jaws.

5. An apparatus for therapeutically irradiating a chosen area with a radiant energy beam as in claim 2 wherein said masking member comprises a first and second pair of spaced, opposed jaws, each of said pair of jaws selectively adjustable as to spacing between its respective jaws and aligned with one another to form said masking member aperture by a common spacing between each of said pair of jaws, and said means for selectively varying the cross-sectional shape of said masking member aperture comprises a mechanism for selectively controlling the spacing between respective jaws of each of said pair of jaws.

6. An apparatus for therapeutically irradiating a chosen area with a radiant energy beam as in claim 5 wherein said mechanism for selectively controlling the spacing between respective jaws of each of said pair of jaws operates independently on each of said pair of jaws to control the spacing between respective jaws of each of said pair of jaws.

7. An apparatus for therapeutically irradiating a chosen area with a radiant energy beam as in claim 2 further including,
    means for selectively varying the cross-sectional shape of said masking member aperture in a predetermined manner as a function of the location of the chosen area and the position of the source of the radiant energy beam.

8. An apparatus for therapeutically irradiating a chosen area with a radiant energy beam as in claim 1 further including,
    means for selectively varying the spatial position of said masking member aperture in a predetermined manner as a function of the location of the chosen area and the position of the source of the radiant energy beam.

9. An apparatus for therapeutically irradiating a chosen area with a radiant energy beam as in claim 1 wherein said masking member is fabricated from a material that attenuates essentially all of the radiant energy passing therethrough.

10. An apparatus for therapeutically irradiating a chosen area with a radiant energy beam as in claim 1 wherein said masking member is fabricated from a material that partially attenuates the radiant energy passing therethrough, but transmits a sufficient amount of the radiant energy for imaging purposes.

11. An apparatus for therapeutically irradiating a chosen area with a radiant energy beam as in claim 1 further including a post-masking member aligned with said masking member aperture and fabricated of a material that attenuates the radiant energy passing therethrough to an energy level essentially uniform with that of the radiant energy passing through said masking member.

12. In combination with a diagnostic computer tomography scanner that uses a radiant energy beam for imaging purposes, an apparatus for therapeutically irradiating a chosen area with the radiant energy beam comprising:
    a masking member fabricated from a material that partially attenuates the radiant energy passing therethrough, but transmits a sufficient amount of the radiant energy for imaging purposes and having an aperture therein adapted for passing an unattenuated portion of the radiant energy beam therethrough;
    means for fastening said masking member to the scanner interposing said masking member in the radiant energy beam intermediate the source of the radiant energy beam and the chosen area for passing said unattenuated portion of the radiant energy beam to irradiate the chosen area;
    means for selectively varying the cross-sectional shape of said masking member aperture in a predetermined manner as a function of the location of the chosen area and the position of the source of the radiant energy beam;

means for selectively varying the spatial position of said masking member aperture in a predetermined manner as a function of the location of the chosen area and the position of the source of the radiant energy beam; and, a post-masking member aligned with said masking aperture and fabricated of a material that attenuates the radiant energy passing therethrough to an energy level essentially uniform with that of the radiant energy passing through said masking member.

13. A method for using a diagnostic computer tomography scanner that uses a radiant energy beam for imaging purposes for therapeutically irradiating a chosen area with the radiant energy beam comprising the steps of:

positioning a patient in the scanner using positioning restraints to prevent patient motion with respect to the scanner;

performing a diagnostic scan of said patient;

determining an area chosen for therapeutic irradiation;

repositioning said patient as necessary to move said chosen area to a selected predetermined location;

measuring the spatial dimensions of said chosen area;

choosing a masking member fabricated from a material that attenuates the radiant energy passing therethrough and having an aperture therein adapted for passing an unattenuated portion of the radiant energy beam therethrough with a cross-sectional beam area essentially equal to that of said chosen area;

interposing said masking member in the radiant energy beam intermediate the source of the radiant energy beam and the chosen area so that said unattenuated portion of the radiant energy beam irradiates the chosen area; and scanning the chosen area through multiple cycles to irradiate the chosen area to a desired exposure level.

14. A method for using a diagnostic computer tomography scanner that uses a radiant energy for imaging purposes for therapeutically irradiating a chosen area with the radiant energy as in claim 13 further comprising the step of:

maintaining in alignment with said masking member aperture a post-making member fabricated of a material that attenuates the radiant energy passing therethrough to an energy level essentially uniform with that of the radiant energy passing through said masking member to permit continued imaging of said patient during irradiation of the chosen area.

15. A method for using a diagnostic computer tomography scanner that uses a radiant energy for imaging purposes for therapeutically irradiating a chosen area with the radiant energy beam as in claim 13 further comprising the step of:

varying selectively the cross-sectional area of said masking member aperture in relation to the location of the chosen area and the source of the radiant energy beam.

16. A method for using a diagnostic computer tomography scanner that uses a radiant energy beam for imaging purposes for therapeutically irradiating a chosen area with the radiant energy beam as in claim 13 wherein the step of positioning said patient as necessary to move said area chosen for irradiation to a selected predetermined position further comprises the step of:

positioning said patient as necessary to move said chosen area to the rotation isocenter of the scanner.

17. A method for using a diagnostic computer tomography scanner that uses a radiant energy beam for imaging purposes for therapeutically irradiating a chosen area with the radiant energy beam as in claim 13 wherein the step of choosing a masking member further includes the steps of:

calculating the desired aperture and attenuation properties of the masking member by using methods of computer tomography reconstruction from projections determined from measuring the spatial dimensions of the chosen area, in conjunction with both the physical principles of radiant energy beam propagation for the scanner, and the physical principles of radiant energy beam attenuation.

18. A method for using a diagnostic computer tomography scanner that uses a radiant energy beam for imaging purposes for therapeutically irradiating a chosen area with the radiant energy beam as in claim 13 wherein the step of scanning the chosen area through multiple cycles further includes the step of:

varying the gantry tilt angles of the scanner through repeated computer tomography scans to therapeutically irradiate a three-dimensional chosen area.

19. A method for using a diagnostic computer tomography scanner that uses a radiant energy beam for imaging purposes for therapeutically irradiating a chosen area with the radiant energy beam as in claim 18 wherein the step of varying the gantry tilt angles of the scanner through repeated computer tomography scans to therapeutically irradiate a three-dimensional chosen area, includes the step of:

applying selected translation motion to the computed tomography scanner table so as to move it into and out of the aperture of the masking member to accompany gantry tilting motion by such calculated distance as to displace the apparent axis of gantry tilt above or below the physical axis of tilting to the location of the chosen area.

20. A method for using a diagnostic computer tomography scanner that uses a radiant energy beam for imaging purposes for therapeutically irradiating a chosen area with the radiant energy beam as in claim 13 wherein the step of scanning the chosen area through multiple cycles further includes the step of:

restricting the radiant energy beams of the scanner to less than the entire diameter of the chosen area.

21. A method for using a diagnostic computer tomography scanner that uses a radiant energy beam for imaging purposes for therapeutically irradiating a chosen area with the radiant energy beam as in claim 13 wherein the step of scanning the chosen area through multiple cycles further includes the step of:

varying the rotating speed of the scanner through repeated computer tomography scans to therapeutically irradiate the chosen area.

22. A method for using a diagnostic computer tomography scanner that uses a radiant energy beam from imaging purposes for therapeutically irradiating a chosen area with the radiant energy beam as in claim 13 wherein the step of scanning the chosen area through multiple cycles further includes the step of:

varying the range of rotation angulation of the scanner through repeated computer tomography scans to therapeutically irradiate the chosen area.

23. A method for using a diagnostic computer tomography scanner that uses a radiant energy beam for imaging purposes for therapeutically irradiating a chosen area with the radiant energy beam as in claim 13 wherein the step of scanning the chosen area through multiple cycles further includes the step of:

varying the translation speed of the scanner through repeated computer tomography scans to therapeutically irradiate the chosen area.

24. A method for using a diagnostic computer tomography scanner that uses a radiant energy beam for imaging purposes for therapeutically irradiating a chosen area with the radiant energy beam as in claim 13 wherein the step of scanning the chosen area through multiple cycles further includes the step of:

varying the range of translation excursion positions and lengths of the scanner through repeated computer tomography scans to therapeutically irradiate the chosen area.

25. A method for using a diagnostic computer tomography scanner that uses a radiant energy beam for imaging purposes for therapeutically irradiating a chosen area with the radiant energy beam as in claim 13 wherein the step of scanning the chosen area through multiple cycles further includes the step of:

varying the radiant energy beam intensity of the scanner through repeated computer tomography scans to therapeutically irradiate the chosen area.

26. A method for using a diagnostic computer tomography scanner that uses a radiant energy beam for imaging purposes for therapeutically irradiating a chosen area with the radiant energy beam as in claim 13 wherein the step of scanning the chosen area through multiple cycles further includes the steps of:

administering a high atomic number element containing a chemical compound which concentrates in the chosen area the radiation energy of the radiant energy beam of the scanner;

timing the scanning of the chosen area using radiant energy beams to achieve photoelectric interaction with the high atomic number element contained within the chemical compound concentrated in the chosen area to therapeutically irradiate the chosen area.

27. A method for using a diagnostic computer tomography scanner that uses a radiant energy beam for imaging purposes for therapeutically irradiating a chosen area with the radiant energy beam as in claim 13 wherein the step of scanning the chosen area through multiple cycles further includes the steps of:

obtaining a gating signal representing those times when the chosen area is situated within a radiant energy beam; and irradiating the chosen area only during such times as such gating signal selects.

* * * * *